United States Patent [19]

Fletcher

[11] 4,435,003
[45] Mar. 6, 1984

[54] CHROMOGENIC QUINAZOLINES

[75] Inventor: Ian J. Fletcher, Magden, Switzerland

[73] Assignee: Ciba-Geigy Corporation, Ardsley, N.Y.

[21] Appl. No.: 421,205

[22] Filed: Sep. 22, 1982

Related U.S. Application Data

[62] Division of Ser. No. 227,294, Jan. 22, 1981.

[30] Foreign Application Priority Data

Jan. 31, 1980 [CH] Switzerland ............................ 780/80
Jul. 15, 1980 [CH] Switzerland .......................... 5411/80

[51] Int. Cl.$^3$ ...................... B41M 5/16; B41M 5/18; B41M 5/22
[52] U.S. Cl. .................................. 282/27.5; 427/151; 428/320.4; 428/320.6; 428/320.8; 428/913; 428/914
[58] Field of Search ............... 282/27.5; 427/151–153; 428/320.4, 320.6, 320.8, 411, 537, 913, 914; 544/80, 117, 119, 282, 284, 289, 293

[56] References Cited

U.S. PATENT DOCUMENTS

| | | |
|---|---|---|
| 3,154,532 | 10/1964 | Weidinger et al. |
| 3,340,260 | 9/1967 | Blatter |
| 3,476,756 | 11/1969 | Taylor et al. |
| 3,574,210 | 4/1971 | Bruer et al. |
| 3,637,693 | 1/1972 | Otterstedt et al. |
| 3,998,951 | 12/1976 | Harnish et al. |
| 4,306,065 | 12/1981 | Chen |

FOREIGN PATENT DOCUMENTS

| | | | |
|---|---|---|---|
| 52-12019 | 1/1977 | Japan | 106/21 |
| 53-101399 | 9/1978 | Japan | 282/27.5 |
| 856158 | 12/1960 | United Kingdom |  |

OTHER PUBLICATIONS

Bischler and Barad, "Zur Kenntnis der Phenmiazin derivative," Ber. 25, 3080–3097, (1892).
Bischler and Howell, "Zur Kenntnis der Phenmiazin derivative," Ber. 26, 1384–1399, (1893).
Armarego, "Quinazolines Part IV, Covalent Hydration in the Cations of Substituted Quinazolines," J. Chem. Soc., 1962, 561–572.

*Primary Examiner*—Bruce H. Hess
*Attorney, Agent, or Firm*—Edward McC. Roberts

[57] ABSTRACT

Chromogenic quinazolines are disclosed. These compounds are particularly suitable for use as color formers in pressure-sensitive or heat-sensitive recording materials and give lightfast yellow, orange and red colorations.

6 Claims, No Drawings

CHROMOGENIC QUINAZOLINES

This is a division of application Ser. No. 227,294 filed on Jan. 22, 1981.

The present invention relates to chromogenic quinazolines, to the production thereof, and to their use as colour formers in pressure-sensitive or heat-sensitive recording materials.

The chromogenic quinazolines of this invention have the general formula

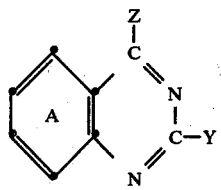

wherein Y is an amino-substituted phenyl radical of the formula

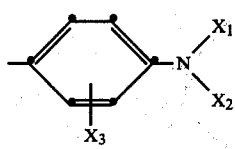

or a 3-carbazolyl radical of the formula

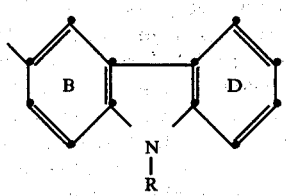

and Z is hydrogen, $R_1$, $-OR_1'$, $-SR_1'$ or $-NH_2R_3$, whilst R is hydrogen, alkyl of at most 12 carbon atoms which is unsubstituted or substituted by halogen, hydroxyl, cyano or lower alkoxy, or is alkenyl of at most 12 carbon atoms, acyl of 1 to 12 carbon atoms, benzyl, or benzyl which is substituted by halogen, nitro, lower alkyl or lower alkoxy; each of $R_1$ and $R_1'$ is alkyl of at most 12 carbon atoms which is unsubstituted or substituted by cyano or lower alkoxy, or is cycloalkyl, unsubstituted or substituted aryl or aralkyl or an unsubstituted or a substituted heterocyclic radical, and $R_1'$ can also be haloalkyl of 2 to 6 carbon atoms; each of $R_2$, $R_3$, $X_1$ and $X_2$ independently is hydrogen, alkyl of at most 12 carbon atoms which is unsubstituted or substituted by halogen, hydroxyl, cyano or lower alkoxy, or is cycloalkyl, phenyl, benzyl, or phenyl or benzyl each of which is substituted by halogen, nitro, cyano, lower alkyl, lower alkoxy or lower alkoxycarbonyl, and $R_2$ is also acyl of 1 to 12 carbon atoms, or each pair of substituents ($R_2$ and $R_3$) and ($X_1$ and $X_2$), together with the nitrogen atom to which said pair is attached, independently is a 5- or 6-membered heterocyclic radical; $X_3$ is hydrogen, halogen, nitro, lower alkyl or lower alkoxy; and each of the rings A, B and D independently is unsubstituted or substituted by cyano, nitro, halogen, lower alkyl, lower alkoxy or lower alkoxycarbonyl, and the ring D can also contain an unsubstituted or a substituted phenyl radical or a fused benzene ring.

In the above definition of the radicals of the quinazoline compounds, the terms "lower alkyl" and "lower alkoxy" usually denote those groups or group constituents which contain 1 to 5, preferably 1 to 3, carbon atoms, e.g. methyl, ethyl, n-propyl, isopropyl, n-butyl, sec-butyl, tert-butyl, or amyl, and methoxy, ethoxy or isopropoxy.

The preferred meaning of aryl is phenyl. "acyl" is preferably formyl, lower alkylcarbonyl, e.g. acetyl or propionyl, or benzoyl. Further acyl radicals are lower alkylsulfonyl, e.g. methylsulfonyl or ethylsulfonyl, as well as phenylsulfonyl. Phenyl, benzyl, and phenylsulfonyl can be substituted by halogen, methyl, methoxy or ethoxy.

Y is preferably an amino-substituted phenyl radical of the formula (1a).

Alkyl groups R, $R_1$, $R_1'$, $R_2$, $R_3$, $X_1$ and $X_2$ can be straight-chain or branched. Examples of such alkyl radicals are: methyl, n-propyl, isopropyl, n-butyl, sec-butyl, n-hexyl, n-octyl or n-dodecyl.

Substituted alkyl radicals R, $R_1$, $R_1'$, $R_2$, $R_3$, $X_1$ and $X_2$ are, in particular, cyanoalkyl or alkoxyalkyl, each containing 2 to 6 carbon atoms, e.g. β-cyanoethyl, β-methoxyethyl or β-ethoxyethyl. $R_1'$ as haloalkyl can be e.g. γ-chloropropyl or, preferably, β-chloroethyl.

R as alkenyl is e.g. allyl, 2-methallyl, 2-ethallyl, 2-butenyl or octenyl.

R and $R_2$ as acyl are e.g. formyl, lower alkylcarbonyl or benzoyl, but the preferred identities are acetyl or propionyl. Benzoyl can be substituted in the benzene ring by halogen, methyl or methoxy.

Cycloalkyl represented by $R_1$, $R_1'$, $R_2$, $R_3$, $X_1$ and $X_2$ is cyclopentyl or, preferably, cyclohexyl.

$R_1$ and $R_1'$ as aralkyl are usually phenylethyl or, preferably, benzyl, whilst aryl is preferably naphthyl, diphenyl and, most preferably, phenyl. The aralkyl and aryl radicals can be substituted by halogen, nitro, lower alkyl, lower alkoxy, lower alkoxycarbonyl or lower alkylcarbonyl.

Examples of preferred substituents in the benzyl and phenyl moiety of the radicals $R_1'$, $R_1$, $R_2$, $R_3$, $X_1$ and $X_2$ are halogens, cyano, nitro, methyl, methoxy or carbomethoxy. Examples of such araliphatic and aromatic radicals are: methylbenzyl, chlorobenzyl, nitrophenyl, cyanophenyl, tolyl, xylyl, chlorophenyl, methoxyphenyl or carbomethoxyphenyl.

A heterocyclic radical represented by $R_1$ and $R_1'$ is, in particular, a 5- or 6-membered heterocyclic ring of aromatic character which preferably contains oxygen, sulfur or nitrogen. Examples of such heterocyclic rings are thienyl, furyl, pyrrolyl, pyrazolyl, imidazolyl or, preferably, pyridyl. These heterocyclic radicals can be substituted, especially by halogen, cyano, nitro, lower alkyl, lower alkoxy or lower alkoxycarbonyl. Preferred heterocyclic radicals $R_1$ and $R_1'$ are 2-furyl, 2-thienyl and, in particular, 2-, 3- or 4-pyridyl.

A heterocyclic radical represented by each of the pairs of substituents ($R_2$ and $R_3$) and ($X_1$ and $X_2$), together with the nitrogen atom to which said pair is attached, is e.g. pyrrolidino, piperidino, pipecolino, morpholino, thiomorpholino or piperazino.

Each of $X_1$ and $X_2$ independently is preferably lower alkyl, benzyl, phenyl or lower alkoxyphenyl. $X_3$ is preferably hydrogen, methyl, methoxy or chlorine. R is preferably $C_1$–$C_8$alkyl or benzyl, and, most preferably, ethyl or butyl.

The rings A, B and D are preferably not further substituted. If they do contain substituents, then each independently is substituted preferably by halogen, lower alkyl or lower alkoxy, e.g. by chlorine, methyl or methoxy. Each benzene ring can advantageously contain 1 or 2 substituents. A substituent of the ring D is preferably in the para-position to the nitrogen. The ring D can also contain one or two fused benzene nuclei which accordingly complete a 1,2-benzocarbazole, 3,4-benzocarbazole or 3,4-dibenzocarbazole ring. Moreover the ring D can contain a phenyl group which may be substituted by halogen, methyl or methoxy.

Important chromogenic quinazolines to be used in the practice of this invention are those of the formula

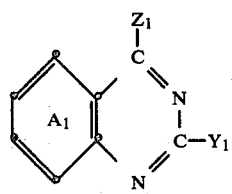

wherein $Y_1$ is an amino-substituted phenyl radical of the formula

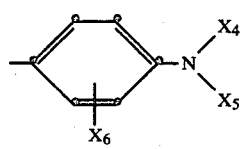

or a 3-carbazolyl radical of the formula

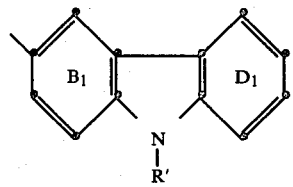

and $Z_1$ is hydrogen, $R_4$, —$OR_4$, —$SR_4$ or —$R_4R_5$, whilst R' is alkyl of at most 12 carbon atoms which is unsubstituted or substituted by halogen, cyano or lower alkoxy, or is lower alkylcarbonyl, or benzyl which is unsubstituted or substituted by halogen, lower alkyl or lower alkoxy; $R_4$ is alkyl of at most 8 carbon atoms which is unsubstituted or substituted by lower alkoxy, or is cyclohexyl, phenyl, naphthyl, benzyl, or phenyl or benzyl each of which is substituted by halogen, nitro, cyano, lower alkyl, lower alkoxy or lower alkoxycarbonyl; each of $R_5$ and $R_6$ independently is hydrogen, lower alkyl, phenyl, lower alkylphenyl, lower alkoxyphenyl or benzyl, and $R_5$ is also lower alkylcarbonyl, lower alkylsulfonyl, benzoyl or phenylsulfonyl; each of $X_4$ and $X_5$ independently is lower alkyl, phenyl, lower alkylphenyl, lower alkoxyphenyl or benzyl, and $X_4$ is also hydrogen; or each pair of substituents ($R_5$ and $R_6$) and ($X_4$ and $X_5$), together with the nitrogen atom to which said pair is attached, independently is pyrrolidino, piperidino, or morpholino; $X_6$ is hydrogen, halogen, lower alkyl or lower alkoxy; and each of the rings $A_1$, $B_1$ and $D_1$ independently can be unsubstituted or substituted by cyano, halogen, lower alkyl or lower alkoxy, and the ring $D_1$ can also contain one or two fused benzene rings.

Preferred quinazolines of the formula (2) are those in which $Y_1$ is an amino-substituted phenyl radical of the formula (2a). $Z_1$ is preferably —$OR_4$, and the preferred meaning of $R_4$ is lower alkyl or phenyl. $R_4$ is also advantageously pyridyl.

Very interesting quinazolines are those of the formulae

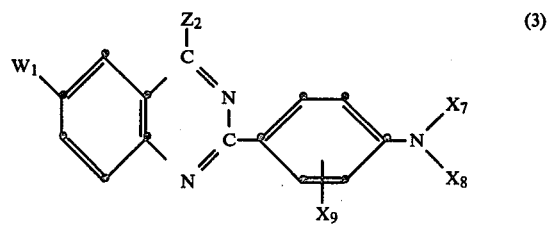

or

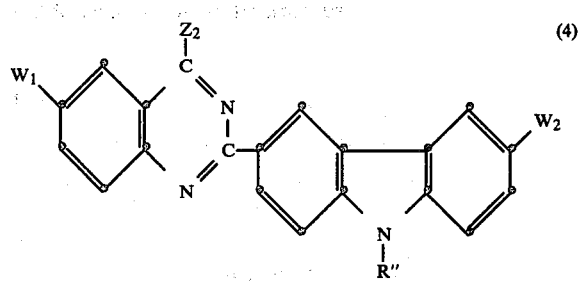

wherein $Z_2$ is hydrogen, $R_7$, —$OR_7$, —$SR_7$ or —$NR_8R_9$, and $R_7$ is lower alkyl, lower alkoxy-lower alkyl, cyclohexyl, phenyl, naphthyl, benzyl, or phenyl which is substituted by halogen, cyano, nitro, methyl or methoxy; each of $R_8$ and $R_9$ independently is hydrogen, lower alkyl, phenyl or benzyl, whilst $R_8$ is also lower alkylcarbonyl or benzoyl; $X_7$ is lower alkyl, phenyl, lower alkylphenyl, lower alkoxyphenyl or benzyl; $X_8$ is hydrogen, lower alkyl, phenyl or benzyl; $X_9$ is hydrogen, methyl, methoxy or ethoxy; R" is alkyl of 1 to 8 carbon atoms or benzyl; and each of $W_1$ and $W_2$ independently is halogen, methoxy, methyl or, preferably, hydrogen.

Preferred quinazolines are those of the formula (3), wherein $Z_2$ is —$OR_7$, and —$OR_7$ is preferably lower alkoxy or phenoxy.

Halogen in connexion with the above substituents in formulae (1) to (4) is e.g. fluorine, bromine, or, preferably, chlorine.

The quinazolines of the formula (1), wherein Z is —$OR_1'$, —$SR_1'$ or —$NR_2R_3$, are obtained by reacting a 4-haloquinazoline compound of the formula

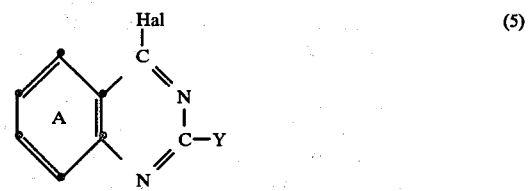

wherein A and Y have the given meanings and Hal is halogen, e.g. bromine, fluorine or, preferably, chlorine, with a compound of the formula

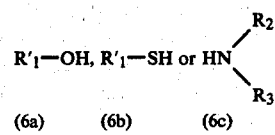

wherein R$_1$', R$_2$ and R$_3$ have the given meanings.

The reaction of the compound of the formula (5) with a compound of the formula (6a), (6b) or (6c) is conveniently conducted in the presence of an acid acceptor, e.g. an alkali metal carbonate or a tertiary nitrogen base such as pyridine or a trialkylamine, if desired in an organic solvent and at reflux temperature.

Examples of suitable solvents are: cycloaliphatic or aromatic hydrocarbons, e.g. cyclohexane, benzene, toluene or xylene; chlorinated hydrocarbons such as chloroform, ethylene chloride or chlorobenzenes; ethers such as diethyl ether or glycol dimethyl ether; cyclic ethers such as dioxane or tetrahydrofurane; as well as dimethyl formamide, diethyl formamide, dimethyl sulfoxide or acetonitrile.

One method of obtaining compounds of the formula (1), wherein Z is hydrogen, consists in dehalogenating the 4-haloquinazoline of the formula (5), under alkaline conditions, to replace the halogen atom by hydrogen. This dehalogenation reaction is carried out e.g. in accordance with J. Chem. Soc. 1962, 561–572, using toluene p-sulfonylhydrazide and with decomposition of the resultant 4-(N-toluene-p-sulfonylhydrazino)quinazoline with an alkali, e.g. sodium hydroxide, preferably in ethylene glycol or ethylene glycol monomethyl ether.

The starting materials of the formula (5) can be obtained by reacting e.g. a 2-aminobenzamide of the formula

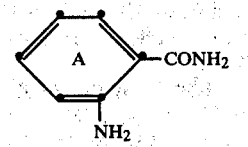

with an aldehyde of the formula

Y—CHO (8)

to give a 1,2,3,4-tetrahydroquinazolin-4-one of the formula

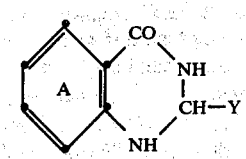

oxidising the compound of the formula (9) to a compound of the formula

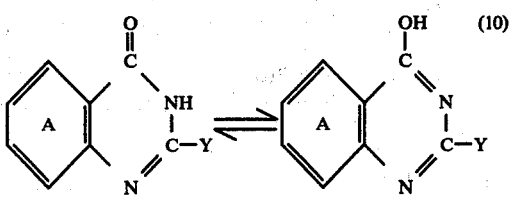

then replacing the hydroxyl group at the heterocyclic ring of the quinazoline system by a halogen atom, e.g. with thionyl chloride in dimethyl formamide, to give the starting material of the formula (5).

The oxidation of the reaction products of the formula (9) to the 4-quinazolines of the formula (10) is carried out with oxidising agents, e.g. chromates, bichromates, chlorates, chlorites, peroxides, e.g. hydrogen peroxide, manganese dioxide, lead dioxide, molecular oxygen, air, perborates, permanganates, chlorine, bromine and, preferably, chloranil.

The best results as regards yield and purity of the 4-quinazolones are obtained with chloranil as oxidising agent, preferably is dimethyl formamide.

A preferred process for obtaining compounds of the formula (1), wherein Z is R$_1$, consists in reacting a ketoamido compound of the formula

wherein A, R$_1$ and Y have the given meanings, with a solution of ammonia in alcohol, preferably in methanol, to give a quinazoline of the formula

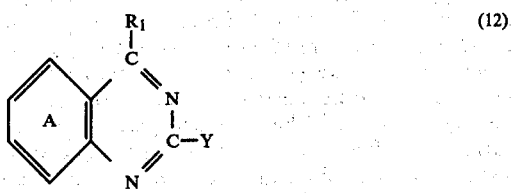

The reaction of the ketoamido compound of the formula (11) with the ammonia solution can be carried out in the temperature range from 80° to 200° C., preferably from 100° to 180° C. Compounds of the formula (11) can be prepared in accordance with the method of A. Bischler and D. Barad, Ber., 25, 3080 (1892) and A. Bischler and F. J. Howell, Ber. 26, 1384 (1893), by acylation of the appropriate ketoamino compounds with the desired acid anhydrides or acid halides.

The quinazolines of the formulae (1) to (4) are normally colourless or faintly coloured. When these colour formers are brought into contact with an acid developer, e.g. an electron acceptor, then, depending on the meaning of Y and Z, they produce intense yellow, orange or red shades of excellent fastness to sublimation and light. They are therefore also very useful when mixed with one or more other known colour formers, for example 2,3-(bis-aminophenyl)-phthalides, 3,3-(bis-indolyl)-phthalides, 3-aminofluoranes, 2,6-diaminofluoranes, leucoauramines, spiropyranes, phenoxazines, phenothiazines or triarylmethane-leuco dyes, to give blue, navy blue, grey or black colorations.

The quinazolines of the formulae (1) to (4) exhibit both on phenolic substrates and especially on clays an improved colour intensity and lightfastness. They are suitable in particular as rapidly developing colour formers for use in a heat-sensitive or especially in a pressure-sensitive recording material, which can also be a copying material.

A pressure-sensitive material consists for example of at least one pair of sheets, which contain at least one colour former of the formulae (1) to (4) dissolved in an organic solvent, and a solid electron acceptor as developer.

Typical examples of such developers are activated clays such as attapulgite, acid clay, bentonite, montmorillonite, activated clay, e.g. acid-activated bentonite or monmorillonite, and also zeolith, halloysite, silica, alumina, aluminium oxide, aluminium phosphate, zinc chloride, kaolin or any clay or acidic organic compound, for example unsubstituted or ring-substituted phenols, salicyclic acid or salicylates and their metal salts, or an acidic polymer, for example a phenolic polymer, an alkylphenolacetylene resin, a maleic acid/rosin resin or a partially or completely hydrolysed polymer of maleic acid and styrene, ethylene or vinyl methyl ether, or carboxypolymethylene. Mixtures of these polymers can also be used. Preferred developers are acid-activated bentonite, zinc salicylates or the condensation products of p-substituted phenols with formaldehyde. These latter can also contain zinc.

The developer can also be used with other basically inert or almost inert pigments. Examples of such pigments are: talcum, titanium dioxide, zinc oxide, chalk, clays such as kaolin, as well as organic pigments, e.g. urea/formaldehyde or melamine/formaldehyde condensates.

The colour former effects a coloured marking at those points where it comes into contact with the electron acceptor. In order to prevent the colour formers contained in the pressure-sensitive recording material from becoming active prematurely, they are usually separated from the electron acceptor. This can conveniently be accomplished by incorporating the colour formers in foamlike, spongelike or honeycomblike structures. Preferably, the colour formers are enclosed in microcapsules, which as a rule can be ruptured by pressure.

When the capsules are ruptured by pressure, for example with a pencil, and the colour former solution is transferred in this manner to an adjacent sheet which is coated with an electron acceptor, a coloured area is produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a polyhalogenated paraffin, such as chloroparaffin, or a polyhalogenated diphenyl, such as trichlorodiphenyl, and also tricresyl phosphate, di-n-butyl phthalate, dioctyl phthalate, trichlorobenzene, trichloroethylphosphate, an aromatic ether such as benzylphenyl ether, a hydrocarbon oil such as paraffin or kerosene, an alkylated derivative of diphenyl, naphthalene or triphenyl, dibenzyl toluene, terphenyl, partially hydrogenated terphenyl, a benzylated xylene, or other chlorinated or hydrogenated, condensed aromatic hydrocarbons. Mixtures of different solvents, especially mixtures of paraffin oils or kerosene and partially hydrogenated terphenyl, are often used in order to obtain an optimum solubility for the colour formation, a rapid and intense coloration, and a viscosity which is advantageous for the microencapsulation.

The capsule walls can be formed evenly around the droplets of the colour former solution by coacervation; and the encapsulating material can consist of gelatin and gum arabic, as described e.g. in U.S. Pat. No. 2,800,457. The capsules can also be formed preferably from an aminoplast or a modified aminoplast by polycondensation, as described in British patent specifications 989,264, 1,156,725, 1,301,052 and 1,355,124. Also suitable are microcapsules which are formed by interfacial polymerisation, e.g. capsules formed from polyester, polycarbonate, polysulfonamide, polysulfonate, but in particular from polyamide or polyurethane.

The microcapsules containing the colour formers of the formula (1) can be used for the production of a wide variety of known kinds of pressure-sensitive copying material. The various systems differ substantially from one another in the arrangement of the capsules, the colour reactants, i.e. the developers, and the support. A preferred arrangement is that in which the encapsulated colour former is in the form of a layer on the back of a transfer sheet and the developer is in the form of a layer on the face of a receiver sheet.

Another arrangement of the components is that wherein the microcapsules which contain the colour former, and the developer, are in or on the same sheet, in the form of one or more individual layers, or are present in the paper pulp.

The capsules are preferably secured to the support by means of a suitable adhesive. As paper is the preferred support, these adhesives are principally paper-coating agents, for example gum arabic, polyvinyl alcohol, hydroxymethyl cellulose, casein, methyl cellulose, dextrin, starch or polymer lattices. These latter are e.g. butadiene/styrene copolymers or acrylic homopolymers or copolymers.

The paper employed comprises not only normal paper made from cellulose fibres, but also paper in which the cellulose fibres are replaced (partially or completely) by synthetic polymers.

The compounds of the formulae (1) to (4) can also be employed as developers in a thermoreactive recording material. This recording material usually contains at least one carrier, one colour former, one electron acceptor and, optionally, also a binder. Thermoreactive recording systems comprise, for example, heat-sensitive recording and copying materials and papers. These systems are used e.g. for recording information, for example in electronic computers, teleprinters or telewriters, or in recording and measuring instruments. The image (mark) formation can also be effected manually with a heated pen. Laser beams can also be used to produce heat-induced marks. The thermoreactive recording material can be composed such that the colour former is dispersed or dissolved in one binder layer and the developer is dissolved or dispersed in the binder in a second layer. Another possibility consists in dispersing both the colour former and the developer in one layer. By means of heat the binder is softened at specific areas and the colour former comes into contact with the developer at those points where heat is applied and the desired colour develops at once.

Suitable developers are the same electron acceptors as are used in pressure-sensitive papers. Examples of developers are the clays and phenolic resins already mentioned, or also the phenolic compounds described e.g. in German Offenlegungsschrift 1,251,348, for example 4-tert-butylphenol, 4-phenylphenol, 4-hydroxydiphenyl ether, α-naphthol, β-naphthol, 4-hydroxymethylbenzoate, 4-hydroxyacetophenone, 2,2'-dihydroxydiphenyl, 4,4-isopropylidenediphenol, 4,4'-isopropylidene-bis-(2-methylphenol), 4,4'-bis-(hydroxyphenyl)-valeric acid, hydroquinone, pyrogallol, phloroglucinol, p-, m- and o-hydroxybenzoic acid, gallic acid, 1-hydroxy-2-naphthoic acid, as well as boric acid and organic, preferably aliphatic, dicarboxylic acids, for example tartaric acid, oxalic acid, maleic acid, citric acid, citraconic acid and succinic acid.

Fusible, film-forming binders are preferably used for the manufacture of the thermoreactive recording material. These binders are normally water-soluble, whereas the quinazolines and the developer are insoluble in water. The binder should be able to disperse and fix the colour former and the developer at room temperature.

By applying heat the binder softens or melts, so that the colour former comes in contact with the developer and a colour is able to form. Examples of binders which are soluble, or at least swellable, in water are e.g. hydrophilic polymers, for example polyvinyl alcohol, polyacrylic acid, hydroxyethyl cellulose, methyl cellulose, carboxymethyl cellulose, polyacrylamide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylmethacrylates, ethyl cellulose, nitrocellulose and polyvinyl carbazole. The preferred arrangement, however, is that in which the colour former and the developer are contained in one layer in a water-soluble binder.

The thermoreactive coatings can contain further ingredients. To improve the degree of whiteness, to facilitate the printing of papers, and to prevent the heated pen from sticking, the coatings can contain e.g. talc, $TiO_2$, ZnO, $CaCO_3$, clays or also organic pigments, for example urea/formaldehyde polymers. In order to effect the colour formation only within a limited temperature range, it is possible to add substances such as urea, thiourea, acetamide, acetanilide, stearyl amide, phthalic anhydride, phthalonitrile or other appropriate fusible products which induce the simultaneous melting of the colour former and the developer. Thermographic recording materials preferably contain waxes, e.g. carnauba wax, paraffin wax or polyethylene wax.

The invention is illustrated by the following Examples, in which percentages are by weight, unless otherwise indicated.

EXAMPLE 1

To a solution of 1.35 g of sodium methylate in 50 ml of methanol are added 2.8 g of 4-chloro-2-(4'-dimethylaminophenyl)quinazoline. The suspension so obtained is stirred for 2½ hours at reflux temperature, then cooled to 5° C. The precipitate is then isolated by filtration, washed with water and dried. This product is then taken up in 20 ml of cold toluene and the toluene solution is evaporated to dryness. Recrystallisation of the residue from methanol yields 1.4 g of a compound of the formula

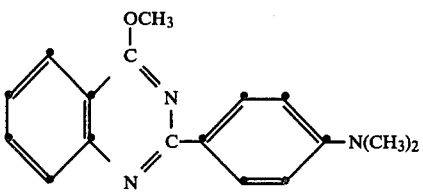

(21)

with a melting point of 94°–95° C. This colour former develops a yellow colour on acid clay.

The 4-chloro-2-(4'-dimethylaminophenyl)quinazoline employed in this Example can be obtained as follows: 13.6 g of anthranilamide and 14.9 g of 4-dimethylaminobenzaldehyde are stirred in 200 ml of ethanol for 2 days at reflux temperature. The mixture is cooled to 20° C. and the precipitate is collected by filtration, washed with ethanol and dried, affording 21.8 g of a compound of the formula

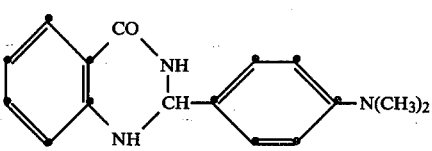

(i)

with a melting point of 214°–217° C.

13.4 g of the compound of the formula (i) are dissolved at 50° C. in 100 ml of dimethyl formamide. The solution is then added dropwise at 50°–55° C. to a suspension of 12.4 g of chloranil in 150 ml of dimethyl formamide which has been preheated to 50° C. The reaction mixture is thereafter stirred for 3 hours, then cooled to 10° C. The precipitated crystals are collected by filtration, washed with ethanol and dried, affording 10.4 g of a compound of the formula

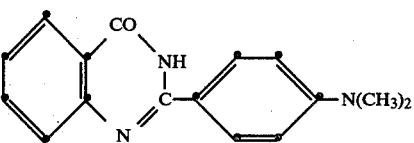

(ii)

with a melting point of 260°–262° C.

5.3 g of the above compound of the formula (ii) are suspended in 30 ml of dimethyl formamide and to the suspension are added 2.5 ml of thionyl chloride with stirring. After stirring for 1½ hours at room temperature, 50 ml of methanol and 5 ml of 80% ammonium hydroxide are added dropwise. The reaction mixture is cooled to 20° C. and the precipitate is collected by filtration, washed with methanol and dried, affording 3.5 g of 4-chloro-2-(4'-dimethylaminophenyl)quinazoline of the formula

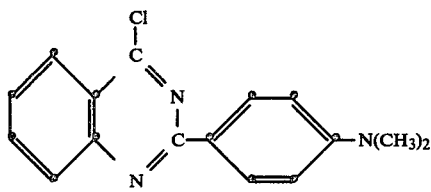

(iii)

with a melting point of 167°–170° C.

EXAMPLE 2

2.8 g of 4-chloro-2-(4'-dimethylaminophenyl)-quinazoline, 15 g of phenol and 2.1 g of anhydrous potassium carbonate are stirred for 45 minutes at 145° C. After cooling to 60° C., 80 ml of a 2 N sodium hydroxide solution are added dropwise to the reaction mixture and stirring is continued for 30 minutes. The precipitate is then collected by filtration, washed with water and dried. Recrystallisation from ethanol yields 1.4 g of a compound of the formula

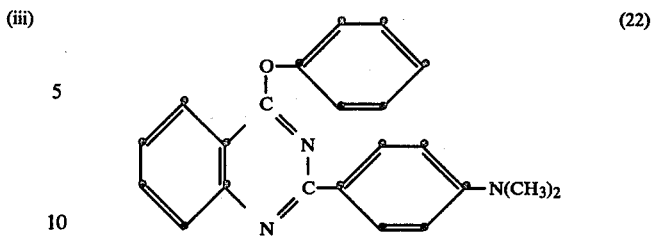

(22)

with a melting point of 187°–189° C. This colour former develops a yellow colour on acid clay.

The colour formers of the formula

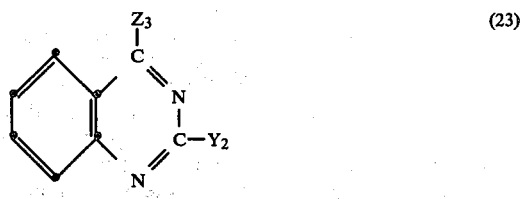

(23)

listed in the following Table are obtained in the same manner as described in either of Examples 1 or 2 using the corresponding starting materials.

TABLE

| Example | $Z_3$ | $Y_2$ | m.p./°C. | Colour on acid clay |
|---------|-------|-------|----------|---------------------|
| 3 | —OCH₂CH₂OCH₃ | —C₆H₄—N(CH₃)₂ | 89–93 | yellow |
| 4 | —OC(CH₃)₃ | —C₆H₄—N(CH₃)₂ | 127–130 | yellow |
| 5 | —OCH₂—C₆H₅ | —C₆H₄—N(CH₃)₂ | 114–115 | yellow |
| 6 | —O—C₆H₄—OCH₃ | —C₆H₄—N(CH₃)₂ | 167–168 | yellow |
| 7 | —O—C₆H₄—Cl | —C₆H₄—N(CH₃)₂ | 146–148 | yellow |
| 8 | —O—C₆H₄—NO₂ | —C₆H₄—N(CH₃)₂ | 175–176 | orange |
| 9 | —O-naphthyl | —C₆H₄—N(CH₃)₂ | 184–185 | yellow |

TABLE-continued

| Example | Z₃ | Y₂ | m.p./°C | Colour on acid clay |
|---|---|---|---|---|
| 10 | $-S-C_6H_4-$ | $-C_6H_4-N(CH_3)_2$ | 162–164 | orange |
| 11 | $-O-C_6H_4-$ | $-C_6H_4-N(CH_3)(C_6H_5)$ | 49–51 | yellow |
| 12 | $-O-C_6H_4-$ | $-C_6H_4-NH-C_6H_4-$ | 118–120 | yellow |
| 13 | $-O-$(pyridyl) | $-C_6H_4-N(CH_3)_2$ | 158–159 | orange |
| 14 | $-O-C_6H_4-$ | $-C_6H_4-N(C_6H_5)_2$ | 79–82 | yellow |
| 15 | $-O-C_6H_4-$ | N-ethylcarbazolyl | 210–211 | yellow |

EXAMPLE 16

2.8 g of 4-chloro-2-(4'-dimethylaminophenyl)-quinazoline are dissolved at 75° C. in 25 ml of dimethyl formamide. To this solution are then added, at 65° C., 2.5 g of a 40% aqueous solution of dimethylamine. The reaction mixture is stirred for 2 hours, then cooled to 5° C. after addition of 25 ml of ethanol. The precipitate is collected by filtration, washed with ethanol and dried, affording 1.9 g of a compound of the formula

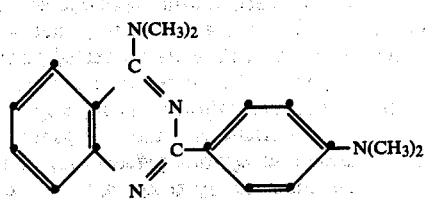

(24)

with a melting point of 154°–156° C.

This colour former develops a yellow colour on said clay.

EXAMPLE 17

The procedure of Example 16 is repeated, replacing dimethylamine by 2.2 g of N-methylaniline. Yield: 0.8 g of a compound of the formula

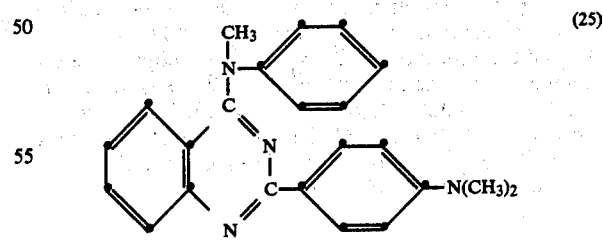

(25)

with a melting point of 165°–167° C.

This colour former develops a yellow colour on acid clay.

EXAMPLE 18

The procedure of Example 16 is repeated, replacing dimethylamine by 0.9 g of morpholine. Yield: 2 g of a compound of the formula

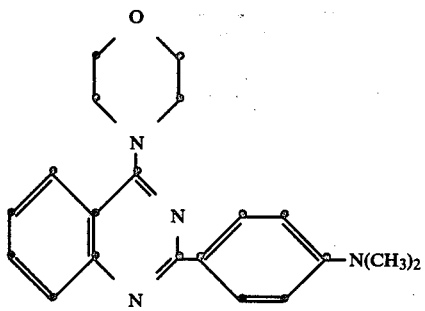

with a melting point of 180°–184° C.

This colour former develops a yellow colour on acid clay.

EXAMPLE 19

2.8 g of 4-chloro-2-(4'-dimethylaminophenyl)-quinazoline are dissolved at 40° C. in 25 ml of chloroform. This solution is cooled to 20° C. and to it is added a solution of 1.9 g of toluene-4-sulfohydrazide in 30 ml of chloroform. The reaction solution is stirred for 18 hours at reflux temperature and then cooled to 10° C. whereupon the precipitate is collected by filtration, washed with chloroform and dried. Then 25 ml of a 1 N sodium hydroxide solution are added dropwise at 90° C. to a suspension of the product in 100 ml of 2-methoxyethanol. After 1 hour at 95° C., the suspension is cooled to 20° C. and then precipitate is isolated by filtration. The filtrate is concentrated and the residue is extracted with methylene chloride. The extract is chromatographed and 0.3 g of a compound of the formula

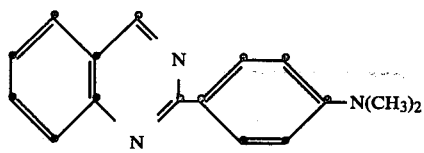

is obtained after recrystallisation from ethanol. Melting point: 136°–137° C.

This colour former develops an orange colour on acid clay.

EXAMPLE 20

9.5 g of 4-diethylaminobenzoyl chloride and 8.85 g of 2-aminobenzophenone are dissolved in 100 ml of toluene and the solution is then stirred for 5 hours at reflux temperature. The toluene is then removed by evaporation. The residue is dissolved in hot methanol and the solution is cooled to 0° C. The precipitated crystals are then collected by filtration and dried, affording 11.6 g of a compound of the formula

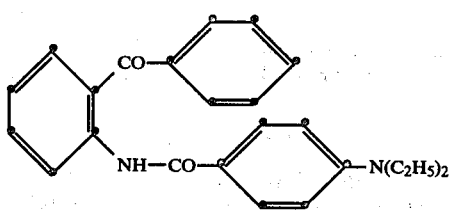

with a melting point of 138°–140° C.

11.5 g of the above compound of the formula (iv) are added to 45 g of a 10% solution of ammonia in methanol, and the mixture is then stirred for 5 hours at 150° C. in an autoclave. After cooling to room temperature, the reaction product is evaporated to dryness and the residue is recrystallised from ligroin. The crystals are dried, yielding 7.4 g of a compound of the formula

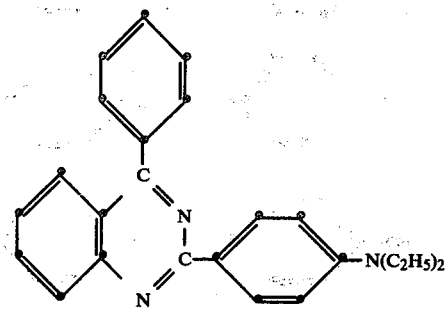

with a melting point of 132°–134° C. This colour former develops a red colour on acid clay.

EXAMPLE 21

The procedure of Example 20 is repeated, replacing 2-aminobenzophenone by 6.1 g of 2-aminoacetophenone. Yield: 5.4 g of a compound of the formula

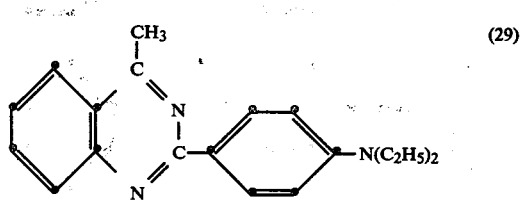

with a melting point of 138°–139° C. This colour former develops an orange colour on acid clay.

EXAMPLE 22 PRODUCTION OF A PRESSURE-SENSITIVE COPYING PAPER

A solution of 3 g of the quinazoline of the formula (22) in 80 g of partially hydrogenated terphenyl and 17 g of kerosene are microencapsulated by coacervation in a manner known per se with gelatin and gum arabic. The microcapsules are mixed with starch solution and coated on a sheet of paper. The face of a second sheet of paper is coated with acid-activated bentonite as colour developer. The first sheet and the sheet coated with the developer are laid on top of each other with the coated sides face to face. Pressure is exerted on the first sheet by writing by hand or typewriter and an intense yellow copy of excellent lightfastness develops immediately on the sheet coated with the developer. Correspondingly intense and lightfast yellow, orange and red copies are also obtained by using each of the other colour formers of the formulae (21) and (23) to (29) as indicated in the Preparatory Examples.

EXAMPLE 23

The procedure of Example 22 is repeated, replacing the quinazoline of the formula (22) by a mixture of the following composition: 1.2 g of 3,3-bis-(4'-dimethylaminophenyl)-6-dimethylaminophthalide, 1.2 g of N-butylcarbazol-3-yl-bis-(4'-N-methyl-N-phenylaminophenyl)methane, 0.4 g of the quinazoline of the formula

(22) and 0.4 g of 3,3-bis-(N-n-octyl-2'-methylindol-3'-yl)phthalide. The so obtained pressure-sensitive recording material gives an intense and lightfast black copy when pressure is exerted by hand or typewriter.

EXAMPLE 24

1 g of the quinazoline of the formula (21) is dissolved in 17 g of toluene. With stirring, 12 g of polyvinyl acetate, 8 g of calcium carbonate and 2 g of titanium dioxide are added to this solution. The resultant suspension is diluted with toluene in the weight ratio 1:1 and applied to a sheet of paper with a knife to a thickness of $10\mu$. On this sheet of paper is laid a second sheet, the underside of which has been coated to a weight of 3 $g/m^2$ with a mixture consisting of 1 part of an amide wax, 1 part of a stearic wax and 1 part of zinc chloride. Pressure is exerted on the top sheet by hand or typewriter and an intense and lightfast yellow copy develops immediately on the sheet coated with the colour former.

EXAMPLE 25: PRODUCTION OF A HEAT-SENSITIVE RECORDING MATERIAL

In a ball mill, 32 g of bis-(4-hydroxyphenyl)-dimethylmethane (bisphenol A), 3.8 g of the distearylamide of ethylenediamine, 39 g of kaolin, 20 g of an 88% hydrolysed polyvinyl alcohol and 500 ml of water are ground to a particle size of about $5\mu$. In a second ball mill, 6 g of the compound of formula (21), 3 g of a 88% hydrolysed polyvinyl alcohol and 60 ml of water are ground to a particle size of about $3\mu$.

Both dispersions are mixed and applied to paper to a dry coating weight of 5.5 $g/m^2$. An intense yellow colour of excellent lightfastness is produced by contacting the paper with a heated ball-point pen. Intense and lightfast yellow, orange and red colorations can also be obtained by using each of the other colour formers of the formulae (22) to (29).

EXAMPLE 26

In a ball mill, 2.7 g of the quinazoline of the formula (22), 24 g of N-phenyl-N'-(1-hydroxy-2,2,2-trichloroethyl)urea, 16 g of stearylamide, 59 g of an 88% hydrolysed polyvinyl alcohol and 58 ml of water are ground to a particle size of 2–$5\mu$. This suspension is applied to a sheet of paper to a dry coating weight of 5.5 $g/m^2$. An intense and lightfast yellow colour is obtained by contacting the paper with a heated ball-point pen.

What is claimed is:

1. A pressure-sensitive or heat-sensitive recording sheet material which contains in its color reactive system, as color former, a quinazoline of the formula

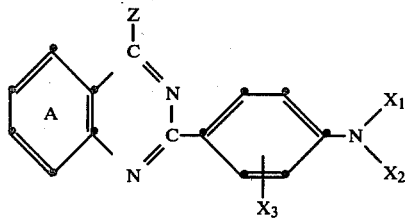

wherein Z is hydrogen, $R_1$, $-OR_1'$, $-SR_1'$ or $-NR_2R_3$; $R_1'$ but not $R_1$ is halo-$C_2$-$C_6$-alkyl or each of $R_1'$ and $R_1$ is $C_1$-$C_{12}$-alkyl, cyano-$C_1$-$C_{12}$-alkyl, lower alkoxy-$C_1$-$C_{12}$-alkyl, cyclopentyl, cyclohexyl, phenyl, halophenyl, nitrophenyl, cyanophenyl, lower alkylphenyl, lower alkoxyphenyl, lower alkoxycarbonylphenyl, lower alkylcarbonylphenyl, diphenyl, halodiphenyl, nitrodiphenyl, cyanodiphenyl, lower alkyldiphenyl, lower alkoxydiphenyl, lower alkoxycarbonyldiphenyl, lower alkylcarbonyldiphenyl, naphthyl, halonaphthyl, nitronaphthyl, cyanonaphthyl, lower alkylnaphthyl, lower alkoxynaphthyl, lower alkoxycarbonylnaphthyl, lower alkylcarbonylnaphthyl, benzyl, halobenzyl, nitrobenzyl, cyanobenzyl, lower alkylbenzyl, lower alkoxybenzyl, lower alkoxycarbonylbenzyl, lower alkylcarbonylbenzyl, phenylethyl, halophenylethyl, nitrophenylethyl, cyanophenylethyl, lower alkylphenylethyl, loweer alkoxyphenylethyl, lower alkoxy carbonylphenylethyl, lower alkylcarbonylphenylethyl, thienyl, halothienyl, cyanothienyl, nitrothienyl, lower alkylthienyl, lower alkoxythienyl, lower alkoxycarbonylthienyl, furyl, halofuryl, cyanofuryl, nitrofuryl, lower alkylfuryl, lower alkoxyfuryl, lower alkoxycarbonylfuryl, pyrrolyl, halopyrrolyl, cyanopyrrolyl, nitropyrrolyl, lower alkylpyrrolyl, lower alkoxypyrrolyl, lower alkoxycarbonylpyrrolyl, pyrazolyl, halopyrazolyl, cyanopyrazolyl, nitropyrazolyl, lower alkylpyrazolyl, lower alkoxypyrazolyl, lower alkoxycarbionylpyrazolyl, imidazolyl, haloimidazolyl, cyanoimidazolyl, nitroimidazolyl, lower alkylimidazolyl, lower alkoxyimidazolyl, lower alkoxycarbonylimidazolyl, pyridyl, halopyridyl, cyanopyridyl, nitropyridyl, lower alkylpyridyl, lower alkoxypyridyl or lower alkoxycarbonylpyridyl; $R_2$ is formyl, lower alkylcarbonyl, lower alkylsulfonyl, benzoyl or phenylsulfonyl or each of $R_2$, $R_3$, $X_1$ and $X_2$ independently is hydrogen, $C_1$-$C_{12}$-alkyl, halo-$C_1$-$C_{12}$-alkyl, hydroxy-$C_1$-$C_{12}$-alkyl, cyano-$C_1$-$C_{12}$-alkyl, lower alkoxy-$C_1$-$C_{12}$-alkyl, cyclohexyl, phenyl, halophenyl, nitrophenyl, cyanophenyl, lower alkylphenyl, lower alkoxyphenyl, lower alkoxycarbonylphenyl, benzyl, halobenzyl, nitrobenzyl, cyanobenzyl, lower alkylbenzyl, lower alkoxybenzyl, lower alkoxycarbonylbenzyl, or $-NR_2R_3$ and $-NX_1X_2$ independently is pyrrolidino, piperidino, pipecolino, morpholino, thiomorpholino or piperazino; $X_3$ is hydrogen, halogen, nitro, lower alkyl or lower alkoxy; and ring A is unsubstituted or substituted by cyano, nitro, halogen, lower alkyl, lower alkoxy or lower alkoxycarbonyl.

2. A pressure-sensitive recording sheet material according to claim 1, which contains the quinazoline dissolved in an organic solvent, and at least one solid electron acceptor.

3. A pressure-sensitive recording sheet material according to claim 1, wherein the quinazoline is encapsulated in microcapsules.

4. A pressure-sensitive recording sheet material according to claim 3, wherein the encapsulated quinazoline is present in the form of a layer on the back of a transfer sheet and the electron acceptor is present in the form of a layer on the face of a receiver sheet.

5. A pressure-sensitive recording sheet material according to claim 1, which contains the quinazoline together with one or more other color formers.

6. A heat-sensitive recording sheet material according to claim 1, which further contains at least one electron acceptor, and at least one binder.

* * * * *